United States Patent
Mueller

(10) Patent No.: US 11,147,991 B2
(45) Date of Patent: *Oct. 19, 2021

(54) TWO-COMPONENT PRODUCTS IN BAGS FOR THE OXIDATIVE DYEING OF KERATIN FIBRES

(71) Applicant: Henkel AG & Co. KGaA, Duesseldorf (DE)

(72) Inventor: Burkhard Mueller, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 887 days.

This patent is subject to a terminal disclaimer.

(21) Appl. No.: 15/537,450

(22) PCT Filed: Nov. 17, 2015

(86) PCT No.: PCT/EP2015/076791
§ 371 (c)(1),
(2) Date: Jun. 19, 2017

(87) PCT Pub. No.: WO2016/096284
PCT Pub. Date: Jun. 23, 2016

(65) Prior Publication Data
US 2017/0354833 A1 Dec. 14, 2017

(30) Foreign Application Priority Data
Dec. 18, 2014 (DE) ...................... 10 2014 226 364.6

(51) Int. Cl.
*A61Q 5/08* (2006.01)
*A61K 8/34* (2006.01)
*A61Q 5/10* (2006.01)
*A61K 8/22* (2006.01)

(52) U.S. Cl.
CPC .................. *A61Q 5/08* (2013.01); *A61K 8/22* (2013.01); *A61K 8/342* (2013.01); *A61Q 5/10* (2013.01); *A61K 2800/88* (2013.01)

(58) Field of Classification Search
None
See application file for complete search history.

(56) References Cited

U.S. PATENT DOCUMENTS

| 4,773,562 A | 9/1988 | Gueret |
| 7,591,862 B2 | 9/2009 | Schmenger et al. |
| 10,137,067 B2 * | 11/2018 | Mueller ................... A61Q 5/08 |
| 2007/0006397 A1 † | 1/2007 | Schmenger |
| 2009/0108021 A1 | 8/2009 | Hansen et al. |
| 2009/0236363 A1 | 9/2009 | Haley et al. |
| 2011/0215113 A1 | 9/2011 | Hansen et al. |
| 2014/0209632 A1 † | 7/2014 | Kuriyama |
| 2016/0128915 A1 † | 5/2016 | Konno |

FOREIGN PATENT DOCUMENTS

| DE | 102007056935 A1 | 5/2009 |
| DE | 102008017104 A1 | 10/2009 |
| EP | 2738117 A1 | 6/2014 |
| WO | 2015028016 A1 | 3/2015 |
| WO | 2015028017 A1 | 3/2015 |
| WO | 2015028018 A1 | 3/2015 |

OTHER PUBLICATIONS

EPO, International Search Report and Written Opinion issued in International Application No. PCT/EP2015/076791, dated Jan. 25, 2016.

\* cited by examiner
† cited by third party

*Primary Examiner* — Jyothsna A Venkat
(74) *Attorney, Agent, or Firm* — Lorenz & Kopf, LLP

(57) ABSTRACT

Products for oxidative dyeing of keratin fibres include at least two preparations (A) and (B) prepared separately. The first preparation (A) includes, in a cosmetic carrier (A1) hydrogen peroxide and (A2) one or more fatty constituents in an amount of from about 0.1 to about 40 wt. % relative to the weight of preparation (A). The second preparation (B) includes, in a cosmetic carrier, (B1) at least one alkalizing agent and (B2) one or more fatty constituents in an amount of from about 0.1 to about 40 wt. % relative to the weight of preparation (B). Preparation (A) is prepared in a first container and preparation (B) is prepared in a second container, both of which containers include at least two layers. An inner layer of first and/or second containers includes a layer of a synthetic polymer (I). An outer layer of first and/or second containers includes a layer of metal.

6 Claims, No Drawings

TWO-COMPONENT PRODUCTS IN BAGS FOR THE OXIDATIVE DYEING OF KERATIN FIBRES

CROSS-REFERENCE TO RELATED APPLICATION

This application is a U.S. National-Stage entry under 35 U.S.C. § 371 based on International Application No. PCT/EP2015/076791, filed Nov. 17, 2015 which was published under PCT Article 21(2) and which claims priority to German Application No. 102014226364.6, filed Dec. 18, 2014, which are all hereby incorporated in their entirety by reference.

TECHNICAL FIELD

The present disclosure relates to the field of cosmetics and relates to products for the oxidative dyeing of keratin fibres, which comprise at least two preparations (A) and (B) prepared separately from one another. Preparation (A) contains hydrogen peroxide and fatty constituents in specific quantitative ranges and preparation (B) contains at least one alkalizing agent and also fatty constituents in specific quantitative ranges. Furthermore, the two preparations (A) and (B) are prepared separately from one another in two containers (A) and (B) which preferably comprise bags and which each comprise at least two layers. The inner layer of each container comprises a synthetic polymer layer whilst the outer layer of each contains each comprises a metal layer which is preferably aluminium foil.

BACKGROUND

The dyeing of keratin fibres, in particular hair, is an important area of modern cosmetics. By dyeing the appearance of the hair can be adapted both to current fashion trends and also to the individual wishes of the individual person. The person skilled in the art is familiar with various possibilities for dyeing hair.

By using semi-permanent dyes, the hair colour can be changed temporarily. In this case, dyes which are already completely formed diffuse from the colorant into the hair fibres. Colouring using semi-permanent dyes is associated with slight damage to the hair but a disadvantage is the low durability and the rapid washing out of colourings obtained using semi-permanent dyes.

If the consumer wishes a long-lasting colour result or a shade which is lighter than his initial hair colour, oxidative dyeing agents are usually used. So-called oxidizing dyes are used for permanent intensive colourings with corresponding authenticity properties. These dyes usually contain oxidizing dye pre-products, so-called developer components and coupler components which form the actual dyes amongst themselves under the influence of oxidizing agents—usually hydrogen peroxide. Oxidizing dyes have exceptional, long-lasting colour results.

Oxidative dyes usually come onto the market in the form of two-component agents in which two different preparations are provided prepared separately in two separate containers and must be mixed with one another shortly before use. The first preparation comprises a formulation—usually adjusted to be acid for stability reasons—which contains hydrogen peroxide in concentrations of from about 1 to about 12 wt. % as oxidizing agent. The oxidizing agent formulation is usually provided in the form of an emulsion or dispersion and is usually provided in a plastic bottle with re-closable outlet opening (developer bottle).

The second preparation comprises a formulation which is adjusted to be alkaline which is frequently present in the form of a cream or gel and which, if a colour change is desired at the same time as the lightening, additionally contains oxidizing dye pre-products. This second component is usually provided in most cases in a tube, more rarely in a plastic container or in a glass bottle.

In order to produce the ready-to-use mixture, the user must mix both preparations together shortly before use. For this purpose, the alkaline cream or gel component is usually transferred from the tube or the glass or plastic container completely into the developer bottle, then both components are mixed together as completely and homogeneously as possible by shaking and finally removed via an outlet opening in the head of the developer bottle.

This separate mixing process however has a number of disadvantages for the consumer. Thus, as a result of the incomplete emptying of the tube, the quantitative ratio of the two components can be changed which leads to deviations in the desired colour result. If the shaking or mixing of the two components is too short, the application mixture is inhomogeneous and the consequence of this is a non-uniform colour result. Furthermore, for reasons of user comfort it is desirable to completely dispense with the mixing step.

In order to avoid these disadvantages, multi-chamber containers with a common outlet opening have been developed in which the two components are mixed in the valve or dispenser during exit. The removal of the application mixture via the dispenser makes any mixing of the components by the user superfluous and has significantly increased the application comfort.

In a particularly convenient embodiment for the user, the multi-chamber containers with common outlet opening comprise an aerosol product. Due to the propellant present in the aerosol product, the two preparations can be removed uniformly in the form of a homogeneous foam by the user by pressing on the valve or the dispenser. Since the two preparations are mixed during removal in the valve or dispenser, a mixing, shaking or agitating by the user which is associated with some effort is no longer required.

The outer shell of very many aerosol containers includes metal. The two preparations to be mixed at the beginning of the oxidative dyeing process contain chemicals which are very reactive, with strong alkalizing agents and oxidizing agents which impose special requirements for the storage and fabrication in the aerosol system. In order to avoid undesirable side reactions (such as, for example, corrosion of the metal aerosol container), these two preparations are therefore not filled directly into two chambers of an aerosol container but are initially filled into two separate bags which are then both located inside the metal aerosol container.

For the removal of the two preparations, usually two tubes connected to the valve project into each bag. Upon actuation of the valve, both preparations are then pressed from each bag by the propellant gas via the two tubes in the direction of the valve, are mixed with one another shortly above or shortly below the valve and then emerge from the valve in the form of the application mixture.

The precise construction of these two-chamber aerosol systems provided with bags is disclosed, for example in EP 2 738 117 A1 or in US 2009/0108021 A, to which reference is made to the full content at this point.

In order to prevent any escape of the contents (in particular the reactive agents) from the bags, the bags usually include at least two layers, an inner polymer layer and an outer metal layer (such as for example aluminium). The outer metal or aluminium layer has a high tightness with respect to gases and prevents the escape of oxygen (which is formed by the decomposition of hydrogen peroxide), the evaporation of water or ammonia and also the escape of all other volatile components such as, for example, solvents.

In order to prevent any direct contact of the preparations with the metal or aluminium foil, an additional polymer layer is applied to the aluminium layers on the inner side of the bag. This inner polymer layer comprises, for example, a layer of a synthetic polyolefin polymer. These two layers can additionally be joined together by an adhesive layer which can include an adhesion polymer. In this case, the bags accordingly comprise at least three layers: an inner layer of a synthetic polyolefin polymer, a middle layer of an adhesion polymer and an outer layer of an aluminium foil.

For further cladding or for protection of the outer metal or aluminium layer, this can be additionally coated or provided with another polymer layer on the outer side. In this case, the bags comprise at least four layers: an inner layer of a synthetic polyolefin polymer, a middle layer of an adhesion polymer, an outer layer of an aluminium foil, and another layer of a synthetic polyolefin polymer right on the outside.

However, even in these multi-chamber aerosol systems provided with bags, the problem exists as before that the mixing ratio of both components can vary depending on the filling level and flow behavior of the formulations in the bags and depending on the pressure inside the chambers of the aerosol container. This carries the great risk that the composition of the application mixture varies in the course of the removal. The associated deviations in the colour result are highly undesired by the user.

So far, it has not been possible to provide oxidative hair colouring products based on a multi-chamber system which allow the metering of the application mixture in a constant, defined composition. In DE 10 2007 956 935 A1, an attempt was made to ensure the constancy of the mixing ratio by developing dispensers with a special control mechanism. However, this mechanism does not eliminate incorrect operation by the user.

Another problem is the stability of the preparations in the bags of the aerosol multi-chamber system since the two layers of inner (polyolefin) polymer and optionally middle adhesion polymer cannot completely prevent the advance of hydrogen peroxide as far as the aluminium foil. If the hydrogen peroxide has then diffused through both polymer layers in an undesirable manner, hydrogen peroxide and aluminium can react with one another, which can result in decomposition of the hydrogen peroxide, the formation of oxygen and inflation of the bag. As a result of these side reactions, the storage stability of preparations comprising hydrogen peroxide in the previously described bags is severely reduced. It was therefore the object of the present disclosure to provide a new product for oxidative dyeing which is based on a multi-chamber aerosol system provided with bags and which enables the long-term storage of a preparation comprising hydrogen peroxide in these bags. In addition, the removal of the finished application mixture from the multi-chamber aerosol system should be defined and constant and should not vary depending on the degree of filling of the bag.

BRIEF SUMMARY

Products for oxidative dyeing of keratin fibres are provided. In an embodiment, a product for oxidative dyeing of keratin fibres includes at least two preparations (A) and (B) that are prepared separately from one another. The first preparation (A) includes, in a cosmetic carrier (A1) hydrogen peroxide and (A2) one or more fatty constituents. The one or more fatty constituents (A2) are present in a total amount by weight (G1) of from about 0.1 to about 40 wt. % relative to the total weight of preparation (A). The second preparation (B) includes, in a cosmetic carrier, (B1) at least one alkalizing agent and (B2) one or more fatty constituents. The (B2) one or more fatty constituents are present in a total amount by weight (G2) of from about 0.1 to about 40 wt. % relative to the total weight of preparation (B). Preparation (A) is prepared in a first container (container A) which includes at least two layers, wherein an inner layer of container A includes a layer of a synthetic polymer (I) and an outer layer of container A includes a layer of metal. Preparation (B) is prepared in a second container (container B) which includes at least two layers, wherein an inner layer of container B includes a layer of a synthetic polymer (I) and an outer layer of container B includes a layer of metal.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It could now be surprisingly found that the previously described object can be solved if a multi-chamber aerosol system is used which contains two separately prepared preparations (A) and (B) in two bags, wherein these two preparations have a content of fatty constituents specially matched to one another.

A first subject matter of the present disclosure is a product for oxidative dyeing of keratin fibres, comprising at least two preparations (A) and (B) prepared separately from one another, wherein a first preparation (A) in a cosmetic carrier contains (A1) hydrogen peroxide and (A2) one or more fatty constituents in a total amount by weight (G1) of from about 0.1 to about 40 wt. % relative to the total weight of preparation (A), the second preparation (B) in a cosmetic carrier contains (B1) at least one alkalizing agent and (B2) one or more fatty constituents in a total amount by weight (G2) of from about 0.1 to about 40 wt. % relative to the total weight of preparation (B), preparation (A) is prepared in a first container (container A) which comprises at least two layers, wherein an inner layer of container A comprises a layer of a synthetic polymer (I) and an outer layer of container A comprises a layer of metal, and preparation (B) is prepared in a second container (container B) which comprises at least two layers, wherein an inner layer of container B comprises a layer of a synthetic polymer (I) and an outer layer of container B comprises a layer of metal.

Keratin fibres, keratin-containing fibres or keratin fibres are to be understood as furs, wool, feathers and in particular human hair. Although the agents as contemplated herein are primarily suitable for lightening and colouring keratin fibres, in principle there is nothing to conflict with a use in other areas.

The preparations (A) and (B) in containers (A) and (B) contain the essential contents in each case in a cosmetic carrier, preferably in a suitable aqueous, alcohol or aqueous-alcohol carrier. For the purpose of oxidative dyeing, these carriers can, for example, be creams, emulsions, gels or tenside-containing foaming solutions such as, for example, shampoos, foam aerosols, foam formulations or other preparations which are suitable for application to the hair. Particularly preferably preparations (A) and/or (B) comprise creams or emulsions.

The term "agents for oxidative dyeing" used as contemplated herein is understood as oxidative dyes which change the colouring of keratin fibres oxidatively, i.e. by using the hydrogen peroxide contained in preparation (A).

If the product as contemplated herein contains no other dyes apart from the hydrogen peroxide, the oxidative dyeing exclusively involves dyeing blond, bleaching or lightening. which is caused by the destruction of the colour pigment intrinsic to the keratin, melanin. In addition, the products as contemplated herein for oxidative dyeing can however also contain one or more oxidizing dye pre-products (of the developer and coupler type). In this case, the hydrogen peroxide contained in the product initiates a dye forming reaction between developer and coupler and the oxidative dyeing is in this case a—more or less strong lightening—and also a colouring. Additionally contained oxidizing dye pre-products are usually prepared together with the alkalizing agent in preparation (B).

The product as contemplated herein comprises at least two preparations (A) and (B) prepared separately from one another.

Characteristic for preparation (A) is its content of (A1) hydrogen peroxide and (A2) one or more fatty constituents in a total amount by weight (G1) of from about 0.1 to about 40 wt. % relative to the total weight of preparation (A).

Hydrogen peroxide (A1) itself or one of its solid addition products with organic and inorganic compounds is used in preparation (A). In particular, the addition products with urea, melamine, polyvinyl pyrrolidinone, sodium carbonate and sodium borate come into consideration as solid addition products as contemplated herein.

Preferably hydrogen peroxide itself is used as an aqueous solution. The concentration of a hydrogen peroxide solution in the agent as contemplated herein is determined on the one hand by the legal specifications and on the other hand by the desired effect: preferably from about 6 to about 12 wt. % solutions in water are used. Preferred preparations (A) as contemplated herein contain—relative to the total weight of preparation (A)—hydrogen peroxide (A1) in a quantity of from about 0.5 to about 20.0 wt. %, preferably from about 1.5 to about 17.0 wt. %, further preferably from about 1.5 to about 15.0 wt. % and particularly preferably of from about 2.5 to about 12.0 wt. %.

In a particularly preferred embodiment, a product as contemplated herein has the first preparation (A) that contains—relative to the total weight of preparation (A)—hydrogen peroxide (A1) in a quantity of from about 0.5 to about 20.0 wt. %, preferably from about 1.5 to about 17.0 wt. %, further preferably from about 1.5 to about 15.0 wt. % and particularly preferably of from about 2.5 to about 12.0 wt. %. The second preparation (B) contains at least one alkalizing agent in a cosmetic carrier.

Preferably the alkalizing agent or agents (B1) can be selected from the group formed from ammonia, alkanol amines, basic amino acids as well as inorganic alkalizing agents such as alkaline (earth) metal hydroxides, alkaline (earth) metal metasilicates, alkaline (earth) alkali metal phosphates and alkaline (earth) metal hydrogen phosphates. Preferred inorganic alkalizing agents are sodium hydroxide, potassium hydroxide, sodium silicate and sodium metasilicate. Organic alkalizing agents which can be used as contemplated herein are preferably selected from monoethanolamine, 2-amino-2-methylpropanol and triethanolamine. The basic amino acids which can be used as alkalizing agents as contemplated herein are preferably selected from the group formed from arginine, lysine, ornithine and histidine, particularly preferably arginine. However, it has been found in the course of investigations for the present disclosure that preferred agents as contemplated herein additionally contain an organic alkalizing agent. In one embodiment the second preparation (B) contains at least one alkalizing agent (B1) selected from the group formed from ammonia, alkanol amines and basic amino acids, in particular of ammonia, monoethanolamine and arginine and/or its compatible salts.

Both preparation (A) and preparation (B) have a content of one or more fatty constituents in specific quantitative ranges. In order to ensure a constant composition of the application mixture during the entire product application period, it is particularly advantageous if the total quantities of the fatty constituents in preparations (A) and (B) are optimally matched to one another. Thus, preparation (A) contains one or more fatty constituents (A2) in a total amount by weight (G1) of from about 0.1 to about 40 wt. %—relative to the total weight of preparation (A). Preparation (B) also contains one or more fatty constituents (B2) in a total amount by weight (G2) of from about 0.1 to about 40 wt. %—relative to the total weight of preparation (B).

"Fatty constituents" are understood as contemplated herein as organic compounds having a solubility in water at room temperature (22° C.) and atmospheric pressure (760 mmHg) of less than about 1 wt. %, preferably of less than about 0.1 wt. %. Explicitly only uncharged (i.e. non-ionic) compounds come under the definition of fatty constituents. Fatty constituents have at least one saturated or unsaturated alkyl group with at least 8 C atoms. The molar weight of the fatty constituents is a maximum of 5000 g/mol, preferably a maximum of 2500 g/mol and particularly preferably a maximum of 1000 g/mol. The fatty constituents do not comprise either polyoxyalkylated or polyglycerylated compounds.

Preferred fatty constituents in this context are understood as constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. In the present disclosure explicitly only non-ionic substances are considered as fatty constituents. Charged compounds such as for example fatty acids and their salts are not considered as fatty constituents.

The $C_{12}$-$C_{30}$ fatty alcohols can comprise saturated, singly or multiply unsaturated, linear or branched fatty alcohols with 12 to 30 C atoms. Examples for preferred linear saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenylalcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z, 12Z)-octadeca-9,12-dien-1-ol (linoleyl alcohol), (9Z, 12Z, 15Z)-octadeca-9,12,15-trien-1-ol (linolenoyl alcohol), gadoleyl alcohol ((9Z)-eicos-9-en-1-ol), arachidonic alcohol ((5Z, 8Z, 11Z, 14Z)-eicosa-5,8,11,14-tetraen-1-ol), erucyl alcohol ((13Z)-docos-13-en-1-ol) and/or brassidyl alcohol ((13E)-docosen-1-ol). The preferred representatives for branched fatty alcohols are 2-octyldodecanol, 2-hexyldodecanol and/or 2-butyldodecanol.

A $C_{12}$-$C_{30}$ fatty acid triglyceride in the present disclosure is understood as the triester of the trivalent alcohol glycerin with three fatty acid equivalents. In this case, both structurally identical and different fatty acids can be involved in the ester formations inside a triglyceride molecule.

Fatty acids are to be understood as contemplated herein as saturated or unsaturated, unbranched or branched, unsubstituted or substituted $C_{12}$-$C_{30}$ carboxylic acids. Unsaturated fatty acids can be singly or multiply unsaturated. In an unsaturated fatty acid, its C—C double bond(s) can have the cis or trans configuration.

The fatty acid glycerides have a particular suitability in which at least one of the ester groups is formed starting from glycerin with a fatty acid, selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z, 11Z, 14Z)-icosa-5,8,11,14-tetraenoic acid] and/or nervonic acid [(15Z)-tetracos-15-enoic acid].

The fatty acid glycerides can also be of natural origin. The fatty acid glycerides occurring in soya oil, peanut oil, olive oil, sunflower oil, macadamia nut oil, moringa oil, apricot kernel oil, marula oil and/or optionally hardened castor oil or mixtures thereof are particularly suitable for use in the product as contemplated herein.

A $C_{12}$-$C_{30}$ fatty acid monoglyceride is understood as the monoester of the trivalent alcohol glycerin with a fatty acid equivalent. In this case, either the middle hydroxy group of the glycerin or the terminal hydroxy group of the glycerin can be esterified with the fatty acid.

The $C_{12}$-$C_{30}$ fatty acid monoglyceride have a particular suitability in which a hydroxy group of the glycerin is esterified with a fatty acid, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z, 11Z,14Z)-icosa-5,8,11,14-tetraenoic acid] and/or nervonic acid [(15Z)-tetracos-15-enoic acid].

A $C_{12}$-$C_{30}$ fatty diglyceride is understood as the diester of the trivalent alcohol glycerin with two fatty acid equivalents. In this case, either the middle or a terminal hydroxy group of the glycerin can be esterified with two fatty acid equivalents or both terminal hydroxy groups of the glycerin are each esterified with a fatty acid. The glycerin here can be esterified with two structurally identical or with two different fatty acids.

The fatty acid diglyceride has a particular suitability in which at least one of the ester groups is formed starting from glycerin with a fatty acid which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid], eleostearic acid [(9Z,11E,13E)-octadeca-9,11,3-trienoic acid], arachidonic acid [(5Z,8Z, 11Z, 14Z)-icosa-5,8,11,14-tetraenoic acid] and/or nervonic acid [(15Z)-tetracos-15-enoic acid].

Hydrocarbons are exclusively compounds including carbon and hydrogen atoms with from 8 to about 150 C atoms. Preferred in this context in particular are aliphatic hydrocarbons such as for example mineral oils, liquid paraffin oils (e.g. paraffinium liquidum or paraffinum perliquidum), isoparaffin oils, semi-solid paraffin oils, paraffin wax, hard paraffin (paraffinum solidum), vaseline and polydecene. Liquid paraffin oils (paraffinium liquidum or paraffinum perliquidum) have proved particularly suitable in this context. Quite particularly preferably the hydrocarbon is paraffinium liquidum, also called white oil. Paraffinium liquidum is a mixture of purified, saturated aliphatic hydrocarbons which for the most part includes hydrocarbon chains with a C chain distribution of from 25 to 35 C atoms.

In a quite particularly preferred embodiment, a product as contemplated herein has the first preparation (A) that contains as fatty constituent(s) one or more compounds from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons, preferably $C_{12}$-$C_{30}$ fatty alcohols and/or hydrocarbons, particularly preferably $C_{12}$-$C_{30}$ fatty alcohols and the second preparation (B) that contains as fatty constituent(s) one or more compounds from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons, preferably $C_{12}$-$C_{30}$ fatty alcohols and/or hydrocarbons, particularly preferably $C_{12}$-$C_{30}$ fatty alcohols.

The fatty constituents in preparations (A) and/or (B) are preferably contained in specific quantitative ranges.

In a further quite particularly preferred embodiment, a product as contemplated herein has the first preparation (A) that contains the fatty constituent(s) in a total amount by weight (G1) of from about 1.0 to about 25 wt. %, preferably from about 3.0 to about 20.0 wt. %, further preferably from about 6.0 to about 17.0 wt. % and particularly preferably from about 8.0 to about 14.0 wt. %—relative to the total weight of preparation (A) and the second preparation (B) that contains the fatty constituent(s) in a total amount by weight (G2) of from about 1.0 to about 25 wt. %, preferably from about 3.0 to about 20.0 wt. %, further preferably from about 6.0 to about 17.0 wt. % and particularly preferably from about 8.0 to about 14.0 wt. %—relative to the total weight of preparation (B).

Preparation (A) which is located in container (A) of the product as contemplated herein contains in a cosmetic carrier one or more fatty constituents in a total amount by weight (G1) of from about 0.1 to about 40 wt. %—relative to the total weight of preparation (A). Preparation (B) which is located in container (A) of the product as contemplated herein contains in a cosmetic carrier one or more fatty constituents in a total amount by weight (G2) of from about 0.1 to about 40 wt. %—relative to the total weight of preparation (B). Here a quite particularly preferred feature of the product is that the weight ratio (G1)/(G2) has a value of form about 0.5 to about 2.0.

The total amount by weight (G1) is understood as the total weight of all the fatty constituents from the aforesaid groups contained in formulation (A). The total weight of preparation (A) forms the calculation basis here.

The total amount by weight (G2) is understood as the total weight of all the fatty constituents from the aforesaid groups contained in formulation (B). The total weight of preparation (B) forms the calculation basis here.

The more precisely preparations (A) and (B) are matched with regard to their fatty constituents, the more reliably and reproducibly the flow behaviors of the two compounds can be matched to one another. If preparations (A) and (B) therefore each contain several different groups of fatty constituents, it is quite particularly advantageous to match the weight ratio of the individual groups of fatty constituents to one another. The matching of the fatty constituents to one another can be quantified by specifying the weight ratio (G1)/(G2). If this is as close to 1 as possible, the quantities of fatty constituents in both preparations (A) and (B) are optimally matched to one another.

In another quite particularly preferred embodiment, a product as contemplated herein has the weight ratio (G1)/(G2) of a value of from about 0.5 to about 2.0, preferably of from about 0.6 to about 1.8, further preferably of from about 0.65 to about 1.7, even further preferably of 0.7 to 1.6 and quite particularly preferably of from about 0.8 to about 1.25.

In order to increase the storage stability of preparation (A), in an explicitly quite particularly preferred embodiment this additionally contains at least one chelating agent from the group (D3) described hereinafter. The chelating agent from group (A3) is added to preparation (A) which also contains hydrogen peroxide (A1).

Chelating agents can also be designated as complexing agents and are compounds which are capable of forming chelates. The term chelate is a collective designation for cyclic compounds in which metals and groups with lone electron pairs are involved in ring formation. This ring formation takes place here by the formation of coordinative bonds of the central metal ion with one or more polydentate ligands, i.e. ligands which have more than one free electron pair.

The chelating agent(s) (A3) contained in preparation (A) are selected from the group of 1-hydroxyethane-1, 1-diphosphonic acid (HEDP), ethylene diamine tetramethylene phosphonic acid (EDTMP),—diethylene triamine pentamethylene phosphonic acid (DTPMP), aminotrimethylene phosphonic acid (ATMP), N,N-bis[2-[bis(carboxymethyl)amino] ethyl]glycin, ethylene diamine-N,N'-disuccinic acid (EDDS), 2-hydroxypropylene diamine-N,N'-disuccinic acid (HPDDS),—ethylene diamine-N,N'-diglutaric acid (EDDG), ethylene diamine-N,N'-bis-(orthohydroxyphenyl) acetic acid (EDDHA) and/or a physiologically compatible salt thereof.

In a further explicitly quite particularly preferred embodiment, a product as contemplated herein has the first preparation (A) that additionally contains (A3) at least one chelating agent from the group of 1-hydroxyethane-1, 1-diphosphonic acid (HEDP), ethylene diamine tetramethylene phosphonic acid (EDTMP), diethylene triamine pentamethylene phosphonic acid (DTPMP), aminotrimethylene phosphonic acid (ATMP), N,N-bis[2-[bis(carboxymethyl)amino] ethyl]glycin, ethylene diamine-N,N'-disuccinic acid (EDDS), 2-hydroxypropylene diamine-N,N'-disuccinic acid (HPDDS), ethylene diamine-N,N'-diglutaric acid (EDDG), ethylene diamine-N,N'-bis-(orthohydroxyphenyl) acetic acid (EDDHA) and/or a physiologically compatible salt thereof.

1-hydroxyethane-1,1-diphosphonic acid (HEDP) is alternatively also designated as etidronic acid, is a compound having the formula (I) and has the CAS number 2809-21-4.

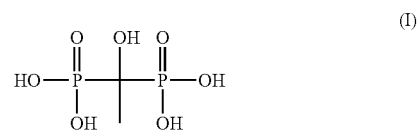

(I)

Suitable physiologically compatible salts of HEDP are for example the mono-, di-, tri- or tetrasodium salt or the mono-, di-, tri- or tetrapotassium salt.

Ethylene diamine tetramethylene phosphonic acid (EDTMP) is a compound having the formula (II), the substance has the CAS No. 1429-50-1.

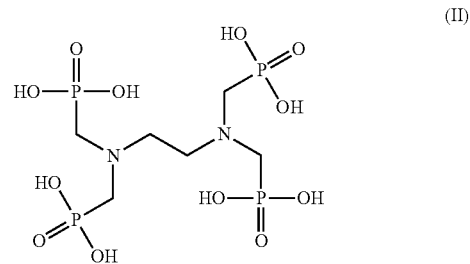 [SMILES: O=P(O)(O)CN(CCN(CP(=O)(O)O)CP(=O)(O)O)CP(=O)(O)O]

(II)

Suitable physiologically compatible salts of EDTMP are for example the mono-, di-, tri- or tetrasodium salt or the mono-, di-, tri- or tetrapotassium salt.

Diethylene triamine pentamethylene phosphonic acid (DTPMP) is a compound having the formula (III), the substance has the CAS No. 15827-60-8.

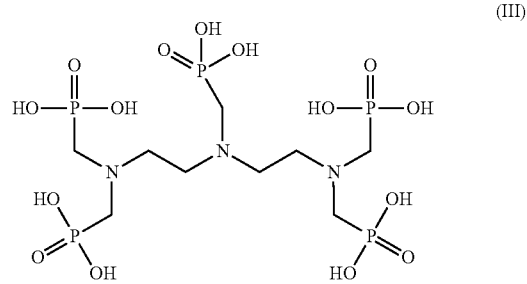 [SMILES: O=P(O)(O)CN(CCN(CP(=O)(O)O)CP(=O)(O)O)CCN(CP(=O)(O)O)CP(=O)(O)O]

(III)

Suitable physiologically compatible salts of DTPMP are the mono-, di-, tri- tetra- and pentasodium salt of this compound, the mono-, di-, tri-, tetra- and pentapotassium salt of this compound.

Aminotrimethylene phosphonic acid (ATMP) is alternatively also designated as nitriolotris(methylene phosphonic acid). ATMP has the formula (IV) and the CAS No. 6419-19-8.

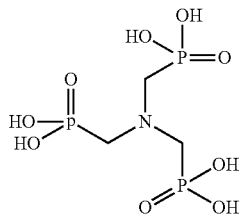
(IV)

Physiologically compatible salts hereof are for example the mono-, di- or trisodium salt of ATMP or the mono-, di- or tripotassium salt of this compound.

N,N-bis[2-[bis(carboxymethyl)amino]ethyl]glycin is a compound having the formula (V). Alternative names for this compound are diethylene triamine penta-acetic acid (DPTA) or also 1,1,4,7,7-diethylene triamine penta-acetic acid. The compound has the CAS No. 67-43-6.

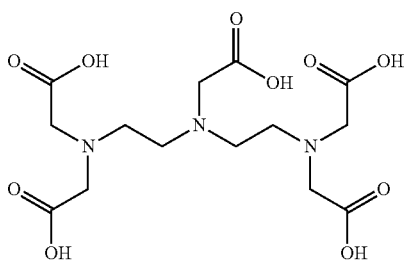
(V)

Suitable physiologically compatible salts hereof are for example the mono-, di-, tri- tetra- or pentasodium salt or the mono-, di-, tri-, tetra- and pentapotassium salt of this compound.

In the case of ethylene diamine-N,N'-disuccinic acid (EDDS), alternatively also designated as ethylene diamine disuccinate, this is a compound having the formula (VI). The compound has the CAS No. 20846-91-7.

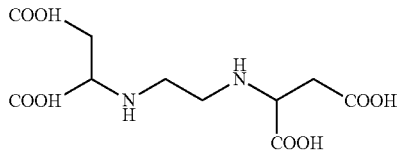
(VI)

A suitable physiologically compatible salt is, for example, the mono-, di-, tri- or tetrasodium salt of this compound or the mono-, di-, tri- or tetrapotassium salt of this compound.

2-hydroxypropylene diamine-N,N'-disuccinic acid (HPDDS) is a compound having the formula (VII)

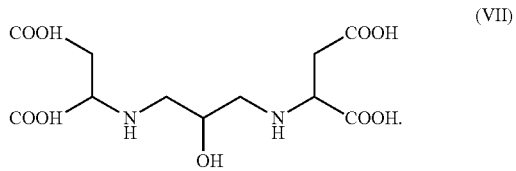 [SMILES: O=C(O)CC(NCC(O)CNC(CC(=O)O)C(=O)O)C(=O)O]
(VII)

A suitable physiologically compatible salt is, for example, the mono-, di-, tri- or tetrasodium salt of this compound or the mono-, di-, tri- or tetrapotassium salt of this compound.

Ethylene diamine-N,N'-diglutaric acid (EDDG) is a compound having the formula (VIII)

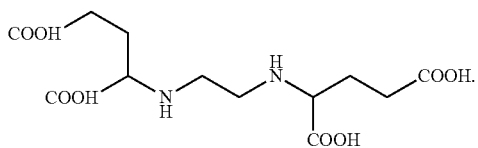
(VIII)

A suitable physiologically compatible salt is, for example, the mono-, di-, tri- or tetrasodium salt of this compound or the mono-, di-, tri- or tetrapotassium salt of this compound.

Ethylene diamine-N,N'-bis-(orthohydroxyphenyl) acetic acid (EDDHA) is a compound having the formula (IX) and has the CAS No. 1170-02-1

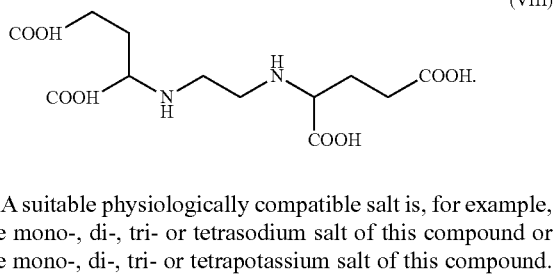
(IX)

In the course of the work leading to the present disclosure, it has been found that the addition of one or more chelating agents having the formulas (I) to (IX) to preparation (A) ensures that preparation (A) which contains hydrogen peroxide (A1) can be stored in a multi-layer container or bag with metal or aluminium outer foil without this resulting in undesirable reactions between the hydrogen peroxide and aluminium foil. In this way, it would be possible to store preparation (A) even for a longer period of several months in a suitable bag. The formation of oxygen and the associated inflation of the container or the bag during the storage time could be severely reduced or even prevented in this way.

In order to optimize the storage stability, the chelating agent or agents from group (A3) are preferably used in certain quantitative ranges in preparation (A). An increase in the storage stability could already be observed with small quantities of chelating agent (A3). However, the reaction of the hydrogen peroxide with the metal foil of the bag could be prevented particularly effectively when the chelating agent(s) were added to preparation (A) in a specific quantitative range. Thus, the chelating agents (A3) in preparation (A)—relative to the total weight of preparation (A)—are used in particular in the range of from about 0.01 to about 5.5 wt. %, preferably from about 0.1 to about 4.5 wt. %, further preferably from about 0.3 to about 3.5 wt. % and particularly preferably from about 0.7 to about 2.5 wt. %. The calculation basis for this quantitative information in wt. % is here the total weight of all the chelating agents from the group (A3) which is related to the total weight of preparation (A).

In a further quite particularly preferred embodiment, a product as contemplated herein has the first preparation (A) that—relative to the total weight of preparation (A)—contains one or more chelating agents (A3) in a total quantity of from about 0.01 to about 5.5 wt. %, preferably from about 0.1 to about 4.5 wt. %, further preferably from about 0.3 to about 3.5 wt. % and particularly preferably from about 0.7 to about 2.5 wt. %.

In order to increase the storage stability of preparation (A) in the container (container A) as contemplated herein, all the chelating agents of formulas (I) to (IX) have proved suitable. In this connection, it has been found however that in particular the chelating agents which have at least one phosphonic acid group are quite particularly well suited. The chelating agents from the group 1-hydroxyethane-1, 1-diphosphonic acid (HEDP), ethylene diamine tetramethylene phosphonic acid (EDTMP), diethylene triamine pentamethylene phosphonic acid (DTPMP), aminotrimethylene phosphonic acid (ATMP), and/or physiologically compatible salts thereof, are particularly effective for increasing the storage stability.

In a further quite particularly preferred embodiment, a product as contemplated herein has preparation (A) that contains—

(A3) at least one chelating agent from the group of 1-hydroxyethane-1, 1-diphosphonic acid (HEDP), ethylene diamine tetramethylene phosphonic acid (EDTMP), diethylene triamine pentamethylene phosphonic acid (DTPMP), aminotrimethylene phosphonic acid (ATMP), and/or physiologically compatible salts thereof. Within this group in turn the chelating agent 1-hydroxyethane-1, 1-diphosphonic acid (HEDP) and the physiologically compatible salts thereof are quite particularly preferred since the best results can be achieved with this chelating agent.

In a further quite particularly preferred embodiment a product as contemplated herein has the first preparation (A) that contains (A3) as chelating agent 1-hydroxyethane-1, 1-diphosphonic acid (HEDP) and/or a physiologically compatible salt thereof.

Furthermore quite particularly preferred is a product as contemplated herein has the first preparation (A) that—relative to the total weight of preparation (A)—contains (A3) 1-hydroxyethane-1, 1-diphosphonic acid (HEDP) and/or the physiologically compatible salts thereof in a total quantity of from about 0.01 to about 5.5 wt. %, preferably from about 0.1 to about 4.5 wt. %, further preferably from about 0.3 to about 3.5 wt. % and particularly preferably from about 0.7 to about 2.5 wt. %.

The chelating agents from group (A3) comprise the compounds of formulas (I) to (IX) and/or the physiologically compatible salts thereof. Physiologically compatible means in this context suitable for use in cosmetic agents (i.e. for application to human hair and human skin). Particularly suitable physiologically compatible salts are sodium salts, potassium salts and/or ammonium salts ($NH_4^+$) of the chelating agents of formulas (I) to (IX).

The amount of hydrogen peroxide used in preparation (A) is determined by the desired lightening effect on the keratin fibre. If only a gentle lightening or predominantly a colouring of the keratin fibres is desired, a hydrogen peroxide content of from about 1.0 to about 2.5 wt. % relative to the total weight of preparation (A) can be sufficient. However, if the keratin fibres are to be lightened more strongly or dyed blonde, a higher content of hydrogen peroxide of, for example up to about 17.0 wt. % (relative to the total weight of preparation (A)) is selected.

In this connection it has been found that the reactions between hydrogen peroxide and the metal or aluminium outer foil of the bag increase with increasing hydrogen peroxide concentration. In order to avoid these reactions, therefore when higher quantities of hydrogen peroxide (A1) are used, a higher quantity of chelating agents from group (A3) should also be selected.

In other words there is a relationship between the quantity of hydrogen peroxide (A1) contained in preparation (A) and the total quantity of chelating agents from group (A3) contained in preparation (A) and the weight ratio (A1)/(A3) should be set to the optimum value to suppress as far as possible all reactions between hydrogen peroxide and the outer metal layer of the container or bag.

It has proved to be particularly advantageous if the weight ratio of the total quantity of hydrogen peroxide (A1) contained in preparation (A) to the total quantity of chelating agents from group (A3) contained in preparation (A), i.e. the weight ratio (A1)/(A3) has a value of from about 1.0 to about 30.0, preferably of from about 2.0 to about 20.0, further preferably of from about 3.0 to about 15.0 and particularly preferably of from about 3.3 to about 13.5.

The calculation basis for all the information in wt. % is here the total quantity of hydrogen peroxide (A1) contained in preparation (A) related to the total weight of preparation (A) and the total quantity of chelating agents from group (A3) contained in preparation (A), related to the total weight of preparation (A).

The weight ratio (A1)/(A3) is then determined by dividing these two quantities.

In a further quite particularly preferred embodiment, a product as contemplated herein has the weight ratio of the total quantity of hydrogen peroxide (A1) that is contained in preparation (A) to the total quantity of chelating agents from group (A3) contained in preparation (A), i.e. the weight ratio (A1)/(A3) with a value of from about 1.0 to about 30.0, preferably of from about 2.0 to about 20.0, further preferably of from about 3.0 to about 15.0 and particularly preferably of from about 3.3 to about 13.5.

By adding further stabilizers (A4), side reactions of hydrogen peroxide with the metal outer layer of the container as contemplated herein can be further suppressed. In particular the addition of 2,6-dipicolinic acid, benzoic acid and/or salicylic acid has proved advantageous in this context. A particularly good inhibition of side reactions could be observed in particular when (A4) 2,6-dipicolinic acid, benzoic acid, salicylic acid and/or physiologically compatible salts of these compounds were present in a total quantity of from about 0.05 to about 4.5 wt. %, preferably from about 0.1 to about 1.0 wt. %, further preferably from about 0.2 to about 0.9 wt. % and particularly preferably from about 0.25 to about 0.7 wt. % in preparation (A). The calculation basis for all the quantitative information is here again the total quantity of the aforesaid compounds (A4) related to the total weight of preparation (A).

In a further quite particularly preferred embodiment, a product as contemplated herein has the first preparation (A) that—relative to the total weight of preparation (A)—additionally contains (A4) 2,6-dipicolinic acid, benzoic acid, salicylic acid and/or physiologically compatible salts of these compounds in a total quantity of from about 0.05 to about 4.5 wt. %, preferably from about 0.1 to about 1.0 wt. %, further preferably from about 0.2 to about 0.9 wt. % and particularly preferably from about 0.25 to about 0.7 wt. %. The physiologically compatible salts of 2,6-dipicolinic acid, benzoic acid and salicylic acid are in particular sodium salts, potassium salts and ammonium salts of the three compounds.

In order to achieve optimal dyeing results, preparations (A) and (B) are preferably set to specific pH values. Preparation (A) which contains hydrogen peroxide is preferably adjusted to be acid for stability reasons and preferably has a pH in the range of from about 1.5 to about 5.0, preferably of from about 2.0 to about 4.5, further preferably of from about 2.2 to about 4.0 and particularly preferably of from about 2.6 to about 3.5. Preparation (B) which contains the alkalizing agent (B1) is on the other hand preferably adjusted to an alkaline range and preferably has a pH in the range of from about 7.5 to about 12.5, preferably of from about 8.5 to about 11.5 and particularly preferably of from about 8.9 to about 10.5.

The ready-to-use dyeing agent which is prepared by mixing preparations (A) and (B) shortly before use is preferably also set to an alkaline pH since a sufficient swelling of the keratin fibres is ensured by alkaline pH values. The dyeing processes on keratin fibres also usually take place in an alkaline milieu. In order to protect the keratin fibres and the skin as far as possible, however it is not desirable to set the pH too high. It is therefore preferable if the pH of the ready-to-use medium has a value of from about 8.0 to about 10.5, further preferably of from about 8.7 to about 10.3, even further preferably of from about 9.0 to about 10.2, and particularly preferably of from about 9.2 to about 10.1. The given pH values are values which were measured at a temperature of 22° C. with a glass electrode.

In a further quite particularly preferred embodiment, a product as contemplated herein has the first preparation (A) that is an aqueous preparation having a pH of from about 1.5 to about 5.0, preferably of from about 2.0 to about 4.5, further preferably of from about 2.2 to about 4.0 and particularly preferably of from about 2.6 to about 3.5 and the second preparation (B) that is an aqueous preparation having a pH of from about 7.5 to about 12.5, preferably of from about 8.5 to about 11.5 and particularly preferably of from about 8.9 to about 10.5.

In preparation (B) the preferably alkaline pH is advantageously adjusted by adding appropriate quantities of the alkalizing agent (B1) as contemplated herein.

Even if preparation (A) is preferably adjusted to be acid, the addition of small quantities of alkalizing agent can be necessary for precise adjustment of the pH. Alkalizing agents which can be used as contemplated herein can be selected from the group formed from ammonia, alkanol amines, basic amino acids as well as inorganic alkalizing agents such as alkaline (earth) metal hydroxides, alkaline (earth) metal metasilicates, alkaline (earth) alkali metal phosphates and alkaline (earth) metal hydrogen phosphates. Preferred inorganic alkalizing agents are sodium hydroxide, potassium hydroxide, sodium silicate and sodium metasilicate. Organic alkalizing agents which can be used as contemplated herein are preferably selected from monoethanolamine, 2-amino-2-methylpropanol and triethanolamine. The basic amino acids which can be used as alkalizing agents as contemplated herein are preferably selected from the group formed from arginine, lysine, ornithine and histidine, particularly preferably arginine.

For example, appropriate quantities of chelating agents from the previously described group (A2) in their respective acid form can be used to adjust the low pH values preferred as contemplated herein. In addition, another one or more additional acids can additionally be used in preparations (A) and/or (B). Suitable acids here are, for example, inorganic acids such as hydrochloric acid, sulphuric acid and/or phosphoric acid. However, organic acids such as for example acetic acid, lactic acid, citric acid, tartaric acid or malic acid can also be used. Preferred in this context in particular are the low-odour organic acids such as lactic acid, citric acid, tartaric acid and/or malic acid.

If the product as contemplated herein is to be used as a pure lightening agent, preparation (B) contains no further dyes. The product as contemplated herein can however comprise an oxidative dye. In this case, further oxidizing dye pre-products of the developer and/or coupler type are added to preparation (B).

Preferred further developer components are selected from p-phenylenediamine, p-toluylene diamine, 2-(2-hydroxyethyl)-p-phenylene diamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol,bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetra-oxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxy-ethyl) pyrazole, 2,4,5,6-tetraaminopyrimidine, 4-hydroxy-2,5,6-triaminopyrimidine, 2-hydroxy-4,5,6-tri-aminopyrimidine, as well as physiologically compatible salts of these compounds. Particularly preferred additional developer components are p-toluylene diamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine and/or 4,5-diamino-1-(2-hydroxyethyl)-pyrazole as well as physiologically compatible salts thereof.

Particularly intensive colourings are delivered by developers from the group of p-phenylenediamine, p-toluylene diamine, 2-(2-hydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis-(2-hydroxy-5-aminophenyl)methane, 4-aminophenol, 4-amino-3-methylphenol, 4,5-diamino-1-(2-hydroxyethyl) pyrazole, 2,4,5,6-tetraaminopyrimidine, 4-hydroxy-2,5,6-triaminopyrimidine and/or 2-hydroxy-4,5,6-triaminopyrimidine. For this reason the use of these developers and/or the physiologically compatible salts thereof is particularly preferred.

In a further embodiment, a product as contemplated herein has the second preparation (B) that contains at least one or more oxidizing dye pre-products from the group formed from p-phenylenediamine, p-toluylene diamine, 2-(2-hydroxy-ethyl)-p-phenylene diamine, N,N-bis-(2-hydroxyethyl)-p-phenylene diamine, 2-methoxymethyl-p-phenylene diamine, N-(4-amino-3-methylphenyl)-N-[3-(1H-imidazol-1-yl)propyl]amine, bis-(2-hydroxy-5-aminophenyl)methane, 4-aminophenol, 4-amino-3-methylphenol, 4,5-diamino-1-(2-hydroxyethyl)-pyrazole, 2,4,5,6-tetraaminopyrimidine, 4-hydroxy-2,5,6-triaminopyrimidine, 2-hydroxy-4,5,6-triamino-pyrimidine and/or physiologically compatible salts thereof.

Coupler components form no significant colouration in the course of oxidative dyeing alone but always require the presence of developer components. Coupler components allow at least one substitution of a chemical group of the coupler by the oxidized form of the developer component. In this case, covalent bonds are formed between coupler and developer components.

Preferably at least one compound from one of the following classes is selected as suitable coupler component as contemplated herein:
  m-aminophenol and/or its derivatives,
  m-diaminobenzene and/or its derivatives,
  o-diaminobenzene and/or its derivatives,
  o-aminophenol derivatives, such as for example o-aminophenol,
  naphthalene derivatives having at least one hydroxy group,
  di- or trihydroxybenzene and/or its derivatives,
  pyridine derivatives,
  pyrimidine derivatives,
  monohydroxyindole derivatives and/or monoaminoindole derivatives,
  monohydroxyindoline derivatives and/or monoaminoindoline derivatives,
  pyrazolone derivatives such as for example 1-phenyl-3-methylpyrazol-5-one,
  morpholine derivatives such as, for example 6-hydroxybenzomorpholine or 6-aminobenzomorpholine,
  quinoxaline derivatives such as 6-methyl-1,2,3,4-tetrahydroquinoxaline.
Mixtures of two or more compounds from one or more of these classes are also contemplated herein within the framework of this embodiment.

Preferred are couplers selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy) propane, 1-methoxy-2-amino-4-(2-hydroxyethylamino)benzene, 1,3-bis(2,4-di-aminophenyl) propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methyl-phenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcin, 2-methylresorcin, 4-chlororesorcin, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindolin, 6-hydroxyindolin and/or 7-hydroxyindolin and physiologically compatible salts thereof.

In a further embodiment, a product as contemplated herein has the second preparation (B) that additionally contains one or more oxidizing dye pre-products from the group formed from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy) propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxy-ethoxy)-5-methylphenylamine, 1-amino-3-bis-(2-hydroxyethyl)aminobenzene, resorcin, 2-methylresorcin, 4-chlororesorcin, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindolin, 6-hydroxyindolin, 7-hydroxyindolin and/or physiologically compatible salts thereof.

Preparation (B) can contain the developers and/or couplers in quantities of from about 0.001 to about 10.0 wt. % relative to the total weight of preparation (B). The quantities used depend in particular on which shade the keratin fibres are to be dyed. For further shading the preparation (B) can also contain one or more semi-permanent dyes from the group of non-ionic, anionic and/or cationic dyes.

Preferred anionic semi-permanent dyes are the compounds known under the international designations or tradenames Bromophenol Blue, Tetrabromophenol Blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic semi-permanent dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31 and Basic Red 51.

In particular, non-ionic nitro and quinone dyes and neutral azo dyes are suitable as non-ionic semi-permanent dyes. Preferred non-ionic semi-permanent dyes are the compounds known under the international designations or tradenames HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Preparations (A) and (B) can furthermore contain additional active substances, adjuvants and additives in order to improve the lightening and/or colouring performance and adjust further desired properties of the agents. For example, one or more of the agents can additionally [contain] non-ionic tensides, anionic tensides, cationic tensides, amphoteric and/or zwitterionic tensides, non-ionic tensides such as for example vinylpyrrolidinone/vinylacrylate copolymers, polyvinylpyrrolidinone, vinylpyrrolidinone/vinylacetate copolymers, polyethylene glycols and polysiloxanes; additional silicones such as volatile or non-volatile, straight-chain, branched or cyclic, cross-linked or non-cross-linked polyalkylsiloxanes (such as dimethicones or cyclomethicones), polyarylsiloxanes and/or polyalkylarylsiloxanes, in particular polysiloxanes with organofunctional groups such as substituted or unsubstituted amines (amodimethicones), carboxyl, alkoxy and/or hydroxyl groups (dimethicone copolyoles), linear polysiloxane(A)-poly-oxyalkylene(B)-block copolymers, grafted silicone polymers; cationic polymers such as quaternized cellulose ether, polysiloxanes with quaternary groups, dimethyldiallyl ammonium chloride polymers, acrylamide dimethyldiallyl-ammonium chloride copolymers, with diethyl sulfate quaternized dimethyl-amino-ethylmethacrylate-vinylpyrrolidinone-copolymers, vinylpyrrolidinone-imidazolinium-methochloride copolymers and quaternized polyvinylalcohol; zwitterionic and amphoteric polymers; anionic polymers such as, for example polyacrylic acids or cross-linked polyacrylic acids; structurants such as glucose, maleic acid and lactic acid, hair-conditioning compounds such as phospholipids, for example lecithin and cephaline; perfume oils, dimethylisosorbide and cyclodextrins; fibre-structure-enhancing active substances, in particular mono-, di- and oligosaccharides such as glucose, galactose, fructose, fruit sugar and lactose; dyes for colouring the agent; anti-dandruff active substancs such as piroctone olamine, zinc omadine and climbazole; amino acids and oligopeptides; animal and/or plant-based protein hydrolysates and in the form of their fatty acid condensation products or optionally anionically or cationically modified derivatives; plant oils; sun protection agents and UV blockers; active substances such as panthenol, pantothenic acid, pantolactone, allantoin, pyrrolidinone carboxylic acids and salts thereof as well as bisabolol; polyphenols, in particular hydroxycinnamic acids, 6,7-dihydroxycumarins, hydroxybenzoic acids, catechins, tannins, leucoanthocyanidins, anthocyanidins, flavanone, flavone and flavonols; ceramides or pseudoceramides; vitamins, provitamins and vitamin precursors; plant extracts; fats and wax such as fatty alcohols, beeswax, montan wax and paraffins; swelling and penetration substances such as glycerin, propylene glycolmonoethylether, carbonates, hydrogen carbonates, guanidine, ureas such as primary, secondary and tertiary phosphates; opacifiers such as latex, styrene/PVP and styrene/acrylamide copolymers; pearl gloss agents such as ethylene glycol mono- and distearate as well as PEG-3-distearate; pigments as well as propellants such as propane butane mixtures, $N_2O$, dimethylether, $CO_2$ and air. In this context reference is expressly made to the known literature, e.g. Kh. Schräder, Principles and Formulations of Cosmetics, 2nd edition, Hüthig Buch Verlag, Heidelberg, 1989, which reproduces the appropriate knowledge of the person skilled in the art.

In preparations (A) and (B) a quite specific viscosity is quite particularly preferably adjusted. The better the viscosities of the two preparations (A) and (B) are matched to one another, the more constant is the composition of the mixture of (A) and (B) upon removal from containers (A) and (B). In this way it is possible to remove defined and constant quantities of preparations (A) and (B) over the entire application time. Furthermore, an application mixture can be removed from the product which has the same composition at every removal step regardless of whether the dispenser is still completely filled or is already partially emptied.

In this context, it has been established that the composition of the application mixture (A)+(B) in particular remains particularly constant if the viscosities (V1) and (V2) are set to quite special ranges.

In a further quite particularly preferred embodiment, a product as contemplated herein has the first preparation (A) that has a viscosity (V1) of from about 2000 to about 80000 mPas, preferably of from about 4000 to about 60000 mPas, further preferably of from about 7000 to about 40000 mPas, even further preferably of from about 8000 to about 35000 mPas and particularly preferably of from about 10000 to about 30000 mPas (22° C./Brookfield viscosimeter/spindle 5/4 rpm) and the second preparation (B) that has a viscosity (V2) of from about 2000 to about 80000 mPas, preferably of from about 4000 to about 60000 mPas, further preferably of from about 7000 to about 40000 mPas, even further preferably of from about 8000 to about 35000 mPas and particularly preferably of from about 10000 to about 30000 mPas (22° C./Brookfield viscosimeter/spindle 5/4 rpm).

The better the viscosities of the two preparations (A) and (B) are matched to one another, the more strongly the content composition of partial quantities of the application mixture which are removed from the two containers (A) and (B) at different time points of the application process is the same.

In a further quite particularly preferred embodiment, a product as contemplated herein has the ratio of the viscosities (V1)/(V2) that has a value of from about 0.5 to about 2.0, preferably of from about 0.6 to about 1.8, further preferably of from about 0.7 to about 1.6, even further preferably of from about 0.8 to about 1.2 and particularly preferably of from about 0.9 to about 1.1.

All the given viscosities comprise viscosities measured at a temperature of 22° C. with a Brookfield viscosimeter using spindle 5 at a revolution speed of 4 rpm.

In the product as contemplated herein, the first preparation (A) is provided prepared in a first container (container A) and the second preparation (B) is provided separately from this prepared in a second container (container B).

A feature for container (A) is that it comprises at least two layers, wherein an inner layer of container A comprises a layer of a synthetic polymer (I) and an outer layer of container A comprises a layer of metal.

A further feature for container (B) is that it comprises at least two layers wherein an inner layer of container B comprises a layer of a synthetic polymer (I) and an outer layer of container B comprises a layer of metal.

The terms "inner layer" and "outer layer" here define the relative position of these two layers with respect to one another. When considering containers (A) and (B) filled with content, the "inner layer" is in each case closer to the content of the container than the "outer layer". The "inner layer" of synthetic polymer (I) is therefore always closer to the respective bag content than the "outer layer" of metal.

The containers (A) and (B) as contemplated herein comprise at least two layers, namely the "inner layer" of synthetic polymer (I) and the "outer layer" of metal. Here the terms "inner layer" and "outer layer" are relative terms but not absolute terms. It is herewith meant that the "inner layer" is only necessarily the "innermost layer" when the contains (A) and (B) comprise precisely two layers. Similarly the "outer layer" is only necessarily the "outermost layer" when the containers (A) and (B) comprise precisely two layers.

If the containers (A) and (B) comprise one or more further layers, these further layers can be localized within the "inner layer", between the "inner and outer layer" and/or outside the "outer layer".

For cost reasons it is preferable if containers (A) and (B) are made of the same material, consequently the two inner layers and the two outer layers of containers (A) and (B) are each the same.

The two containers (A) and (B) quite particularly preferably comprise bags. Preferably two identical bags are used as containers (A) and (B). The total layer thickness of these bags is preferably a thickness of from about 2 to about 400 μm (micron), preferably of from about 10 to about 250 μm (micron) and particularly preferably of from about 50 to about 200 μm (micron).

In a further quite particularly preferred embodiment, a product as contemplated herein has
the first container (container A) that is a bag having a total layer thickness of from about 2 to about 400 μm (micron), preferably of from about 10 to about 250 μm (micron) and particularly preferably of from about 50 to about 200 μm (micron) and/or
the second container (container B) that is a bag having a total layer thickness of from about 2 to about 400 μm (micron), preferably of from about 10 to about 250 μm (micron) and particularly preferably of from about 50 to about 200 μm (micron).

In a further quite particularly preferred embodiment, a product as contemplated herein has
the first container (container A) that is a bag having a total layer thickness of from about 50 to about 200 μm (micron) and
the second container (container B) that is a bag having a total layer thickness of from about 50 to about 200 μm (micron).

The total layer thickness is understood as the sums of the layer thicknesses of all the individual layers present in the bag.

The inner layer of containers (A) and (B) which comprises a layer of a synthetic polymer in each case preferably comprises a layer of a polyolefin polymer such as for example a "low density" polyethylene (LDPE), a "medium density" polyethylene (MPDE), a "high density" polyethylene (HDPE), a linear "low density" polyethylene (LLDPE), a linear "very low density" polyethylene (LVLDPE), an isotactic or syndiotactic polypropylene (PP), an ethylene propylene copolymer, a 1-polybutene polymer, an ethylene/1-butene copolymer, a propylene/1-butene copolymer or an ethylene/propylene/1-butene copolymer.

Within this group the linear "low density" polyethylene (LLDPE) is particularly preferred. The density of the linear "low density" polyethylene is preferably from about 0.91 to about 0.94 g/cm$^3$.

In a further quite particularly preferred embodiment, a product as contemplated herein has
the inner layer of container (A) that comprises a layer of a synthetic polymer (I) from the group of polyolefins, preferably of polyethylene, polypropylene, a polyethylene/polypropylene copolymer, poly-1-butene, a polyethylene/poly-1-butene copolymer, a polypropylene/poly-1-butene copolymer and/or a polyethylene/polypropylene/poly-1-butene copolymer and/or
the inner layer of container (B) that comprises a layer of a synthetic polymer (I) from the group of polyolefins, preferably of polyethylene, polypropylene, a polyethylene/polypropylene copolymer, poly-1-butene, a polyethylene/poly-1-butene copolymer, a polypropylene/poly-1-butene copolymer and/or a polyethylene/polypropylene/poly-1-butene copolymer.

In an explicitly quite particularly preferred embodiment, a product as contemplated herein has
the inner layer of container (A) that comprises a layer of a synthetic polymer (I) comprising polyethylene and
the inner layer of container (B) that comprises a layer of a synthetic polymer (I) comprising polyethylene.

In containers (A) and (B) the inner layer of the containers of synthetic polymer (I) can comprise a layer thickness of from about 20 to about 200 μm (micron), preferably of from about 40 to about 150 μm (micron) and particularly preferably of from about 50 to about 80 μm (micron).

In a further quite particularly preferred embodiment, a product as contemplated herein has
the inner layer of container A that comprises a layer of synthetic polymer (I) having a layer thickness of from about 20 to about 200 μm (micron), preferably of from about 40 to about 150 μm (micron) and particularly preferably of from about 50 to about 80 μm (micron) and/or
the inner layer of container B comprises a layer of synthetic polymer (I) having a layer thickness of from about 20 to about 200 μm (micron), preferably of from about 40 to about 150 μm (micron) and particularly preferably of from about 50 to about 80 μm (micron).

The outer layer of containers (A) and (B) comprises a layer of metal in each case, this metal quite particularly preferably comprises aluminium for example an aluminium foil. The aluminium foil in each case has a preferred layer thickness of from about 5 to about 50 μm, preferably of from about 7 to about 25 μm and particularly preferably of from about 7 to about 12 μm.

In a further particularly preferred embodiment, a product as contemplated herein has
the outer layer of container (A) that comprises a layer of aluminium having a layer thickness of from about 5 to about 50 μm, preferably of from about 7 to about 25 μm and particularly preferably of from about 7 to about 12 μm and/or
the outer layer of container (B) that comprises a layer of aluminium having a layer thickness of from about 5 to about 50 μm, preferably of from about 7 to about 25 μm and particularly preferably of from about 7 to about 12 μm.

In a further particularly preferred embodiment, a product as contemplated herein has
the outer layer of container (A) that comprises a layer of aluminium having a layer thickness of from about 5 to about 50 μm, preferably of from about 7 to about 25 μm and particularly preferably of from about 7 to about 12 μm and/or
the outer layer of container (B) that comprises a layer of aluminium having a layer thickness of from about 5 to about 50 μm, preferably of from about 7 to about 25 μm and particularly preferably of from about 7 to about 12 μm.

The two containers (A) and (B) can additionally comprise another one or more layers of at least one further polymer (II) which is structurally different from the synthetic polymer (I).

In a further particularly preferred embodiment, a product as contemplated herein has containers (A) and/or (B) that comprise a third layer of a synthetic polymer (II) which is structurally different from synthetic polymer (I).

This third layer can, for example, comprise a layer of an adhesive or adhesion polymer localized between the inner layer of synthetic polymer (I) (preferably polyethylene) and outer metal layer (preferably aluminium). Beginning in the interior of the containers (A) and (B), the sequence of the layer is then: inner layer of synthetic polymer (I) (preferably polyethylene)—middle layer of synthetic polymer (II) (adhesion polymer)—outer layer of metal (preferably aluminium foil).

A suitable adhesion polymer (i.e. a synthetic polymer (II)) for example is a polyurethane copolymer which can be produced by reaction of an isocyanate with a polyol. Preferably this polyurethane copolymer is cross-linked or highly cross-linked. As isocyanates it is possible to use, for example, 1,6-hexamethylene diisocyanates, 2,2,4-trimethyl-hexamethylene diisocyanate and lysine ester diisocyanates, aliphatic polyisocyanates as well as hydrogenated diphenylmethane diisocyanate, isophorone diisocyanate or hydrogenated tolylene diisocyanate, or aromatic polyisocyanates such as, for example tolylene diisocyanate, 4,4'-diphenylmethane diisocyanate, naphthalene diisocyanate, xylene diisocyanate, triphenylmethane diisocyanate and tris(4-phenylisocyanate)thiophosphate.

Polyols which can be used in the polymerization are for example oxiranes such as ethylene oxide, propylene oxide, butylene oxide or also tetrahydrofuran or ethylene glycol, propylene glycol, trimethylolpropane or glycerin.

Alternatively the third layer in containers (A) and (B) can also comprise a layer of a synthetic polymer (II) from the group of polyester, polyamide, polyethylene terephthalates, polybutylene terephthalates and polyolefins different from the polymer (I).

In a further preferred embodiment, a product as contemplated herein has the third layer of container (A) that comprises a layer of a synthetic polymer (II) from the group of polyurethanes, polyester, polyamides, polyethylene terephthalates, polybutylene terephthalates and polyolefins different from polymer (I) and/or the third layer of container (B) that comprises a layer of a synthetic polymer (II) from the group of polyurethanes, polyester, polyamides, polyethylene terephthalates, polybutylene terephthalates and polyolefins different from polymer (I).

In a further preferred embodiment, a product as contemplated herein has containers (A) and (B) that have a third layer of a synthetic polymer (II) which is structurally different from the synthetic polymer (I), wherein the third layer of container (A) comprises a layer of a synthetic polymer from the group of polyurethanes, polyester, polyamides, polyethylene terephthalates, polybutylene terephthalates and polyolefins different from polymer (I) and/or the third layer of container (B) comprises a layer of a synthetic polymer from the group of polyurethanes, polyester, polyamides, polyethylene terephthalates, polybutylene terephthalates and polyolefins different from polymer (I).

With reference to all further details for the polymer layer thicknesses, layer sequences and layer materials of containers (A) and (B), reference is made to the full content of EP 2 738 117 A1. The presence of further layers of additional polymers can slow the diffusion of hydrogen peroxide through these polymer layers, possibly inhibit it to a certain degree and thus reduce the reaction between hydrogen peroxide and the outer aluminium layer of the bag. A further quite particularly preferred embodiment has the containers (A) and (B) that comprise layers of at least 3, preferably of at least 4, further preferably of at least 5, even further preferably of at least 6 and quite particularly preferably of at least 7 different materials.

In a further quite particularly preferred embodiment, a product as contemplated herein has container (A) that comprises layers of at least 3, preferably of at least 4, further preferably of at least 5, even further preferably of at least 6 and quite particularly preferably of at least 7 different materials and/or container (B) that comprises layers of at least 3, preferably of at least 4, further preferably of at least 5, even further preferably of at least 6 and quite particularly preferably of at least 7 different materials.

In a further quite particularly preferred embodiment, a product as contemplated herein has container (A) that comprises layers of at least 3, preferably of at least 4, further preferably of at least 5, even further preferably of at least 6 and quite particularly preferably of at least 7 different materials and/or container (B) that comprises layers of at least 3, preferably of at least 4, further preferably of at least 5, even further preferably of at least 6 and quite particularly preferably of at least 7 different materials.

Different layers are understood in the present disclosure as layers of different materials, i.e. layers of different polymers and metals.

In a quite particularly preferred embodiment, the product as contemplated herein comprises two bag-shaped containers (A) and (B) which each contain preparations (A) and (B) and which are together located in an aerosol pressure container (C). In this embodiment the aerosol pressure container has an outlet opening (D) which is connected to container (A) and container (B).

In a further explicitly quite particularly preferred embodiment, a product as contemplated herein has the first container (container A) and the second container (container B) that are together located inside an aerosol pressure container (C), the aerosol pressure container (C) that has an outlet opening (D) which is connected to container (A) and to container (B) and the space between the outer walls of the two containers (A) and (B) and the inner wall of the aerosol pressure container (C) is filled with at least one propellant gas.

Preparations (A) and (B) are prepared separately in containers (A) and (B) but can be brought into contact via the outlet opening (D). As long as the outlet opening (e.g. the valve) is not actuated, preparations (A) and (B) are separate and contact between the two preparations is only made by actuating the outlet opening (D).

Containers (A) and (B) can be arranged inside the aerosol pressure container (C) next to, above or below one another. The capacity of containers (A) and (B) can be from about 10 $cm^3$ to about 1000 $cm^3$ each and the capacity of containers (A) and (B) can be the same or different. Preferably the capacity of containers (A) and (B) is the same. The aerosol pressure container (C) has an outlet opening (D) which is connected to the two containers (A) and (B). During removal the two preparations (A) and (B) are removed simultaneously via the common outlet opening and only mixed together in or directly after the outlet opening (D). Thus, preparations (A) and (B) only come into contact and form the ready-to-use dye during or directly after passing through the outlet opening (D).

The outlet opening (D) can for example comprise a valve and the preparations (A) and (B) are removed via the common outlet opening (D) by pressing the valve.

In a further preferred embodiment, a product as contemplated herein has the first container (container A) and the second container (container B) that are together located inside an aerosol pressure container (C), the aerosol pressure container (C) that has an outlet opening (D) which is connected to container (A) and to container (B) and the space between the outer walls of the two containers (A) and (B) and the inner wall of the aerosol pressure container (C) is filled with at least one propellant gas from the group propane, propene, n-butane, iso-butane, iso-butene, n-pentane, pentene, iso-pentane, iso-pentene, air, nitrogen, argon, $N_2O$ and/or $CO_2$.

In the aforesaid embodiment the product as contemplated herein comprises an outer compressed gas container. Possible compressed gas containers comprise containers made of metal (aluminium, tin plate, tin), protected or non-splintering plastic or made of glass which is coated with plastic on the outside, for which compressive strength and breaking strength, corrosion resistance, easy filling and also aesthetic aspects, handiness, printability etc. also play a part. Particularly preferred compressed gas containers are containers made of metal (aluminium, tin plate, tin).

As described previously, the two separate containers (A) and (B) preferably comprise two deformable bags, preferably made of aluminium laminated with a synthetic polymer (I) which are each connected to the outlet opening (D). The outlet opening (D) comprises a pressure container dispensing device. Both bags are located in a can-shaped pressure container wherein the pressure container together with the pressure container dispensing device seals the product in a pressure-tight manner towards the outside. The space between the outer wall of the bag and the inner wall of the pressure container is filled with at least one propellant gas. Corresponding dispensers are also known from US 2009/0108021 A1.

Particularly good effects as contemplated herein are achieved if the internal pressure of the pressure container is at least 1.8 bar, in particular at least 2.5 bar. These specified and preferred internal pressures relate to the internal pressures prevailing in the completely filled aerosol pressure container (C). This pressure decreases as removal of preparations (A) and (B) progresses.

The product further comprises a dispensing device (corresponding to outlet opening D) which can have a valve for dispensing the application mixture. In a preferred embodiment as contemplated herein the valve comprises a valve plate coated with a varnish or a polymeric plastic and an exactly the same flexible element with restoring characteristic which rests the valve into the closed position (=rest position of the valve) after the end of actuation. Corresponding cosmetic products in which the aerosol dispensing device comprises a valve which has a valve cone and/or a flexible element with restoring characteristic which is/are coated with a varnish or a polymeric plastic are also preferred as contemplated herein.

In a further preferred embodiment as contemplated herein, the flexible element with restoring characteristic can be configured as a helical spring or coil compression spring. In a further preferred embodiment as contemplated herein, the flexible element of the valve with restoring characteristic can be configured in one piece with the valve cone and have resilient legs. This spring can be made of metal or plastic.

All the valves used as contemplated herein preferably have an internally varnished valve plate, wherein varnish and valve material are compatible with one another. If aluminium valves are used as contemplated herein, their valve plates can be coated on the inside, e.g. with Micoflex varnish. If tin plate valves are used as contemplated herein, their valve plates can be coated on the inside e.g. with PET (polyethyleneterephthalate). The containers used which, for example can be made of tin plate or aluminium, where aluminium containers are preferred as contemplated herein, must be varnished or coated on the inside in view of the corrosivity of the water used as contemplated herein in oil emulsions.

If the product as contemplated herein is applied via a pressure container, the dispensers additionally contain at least one propellant gas from the group propane, propene, n-butane, iso-butane, iso-butene, n-pentane, pentene, iso-pentane, iso-pentene, air, nitrogen, argon, $N_2O$ and/or $CO_2$. Within this group the permanent gases air, nitrogen, argon, $N_2O$ and/or $CO_2$ are preferred, with nitrogen, argon and/or $CO_2$ being quite particularly preferred.

Furthermore, it has proved to be preferable if the propellant gases are contained at certain pressures in the aerosol pressure container (C). In a preferred embodiment, the aerosol pressure containers (C) as contemplated herein therefore contain one or more additional propellant gases having a pressure of from about 3-12 bar, preferably of from about 4 to about 10 bar, and particularly preferably of from about 5 to about 8 bar—in each case relative to the pressure of the propellant gases between the bag-shaped containers (A) and (B) and the pressure container.

Preferably the individual product compositions are mixed to a complete formulation in the course of the product applications in order to exhaust the complete effectiveness of the complete formulation in this way and generally facilitate the application of the product. For this purpose, in addition to containers (A) and (B), the dispenser appropriately comprises a dispensing head inside which preparations (A) and (B) are conveyed from the chambers to the outlet opening (D). A suitable mixing device is formed in the dispensing head which ensures the desired thorough mixing of the preparations (A) and (B) upstream of the outlet opening (D) before the thoroughly mixed complete formulation, i.e. (A)+(B) is dispensed via the outlet opening (C). Known from DE 3729491 A1 for example is a generic dispenser with a comparable mixing device where the mixing device there however only has a very short mixing section. As contemplated herein, such a mixing device is integrated structurally directly in the dispensing head or alternatively is arranged as a separate component inside the dispensing head. Suitable mixing devices as contemplated herein are to be understood, for example, as static mixers or comparably acting mixing sections through which the flowable preparations (A) and (B) flow and are mixed in the course of this through-flow. For this purpose such a mixing section usually has suitable flow inserts or flow disturbers which bring about a thorough mixing of individual fluid components during flow as a result of resulting turbulence. A decisive factor for the quality of the thorough mixing of individual fluid components, here the preparations (A) and (B), inside the mixing device is inter alia the specific matching of the length of the mixing section and the shape of the flow inserts to the rheological properties of the preparations (A) and (B). Usually defined minimum lengths of the mixing section are required for satisfactory mixing results of the mixing device as contemplated herein. The mixing section of the mixing device as contemplated herein is therefore preferably configured in such a manner that a defined minimum length of the mixing section is guaranteed without abandoning a compact overall construction of the mixing device and therefore of the dispensing head. Thus, satisfactory mixing results are ensured and at the same time desired compact external dimensions of the mixing device and the dispensing head are ensured. To this end the mixing section is configured to be spiral or comparatively compact inside the dispensing head.

The choice of volumes of the individual containers (A) and (B) is determined by the desired ratio of the volumes of preparation (A) and preparation (B). Preferably the volumes of the chambers (A) and (B) are the same.

The quantitative ratio of preparation (A) to the quantity of preparation (B) as contemplated herein is preferably in a range of from about 1:2 to about 3:1, a range of from about 1:1.5 to about 1.5:1 is preferred as contemplated herein and a quantitative ratio of 1:1 is particularly preferred.

The products as contemplated herein can be used in methods for oxidative changing of hair colour. These methods are characterized for the user by particular application comfort since the laborious and error-prone production of application mixtures by the user is omitted. In addition, a particularly uniform colour result can be achieved by application of the products since as a result of the special rheological matching of formulations (A) and (B), it is possible to remove the two formulations in precisely defined always the same quantitative fractions during the entire application process.

With reference to further preferred embodiments of the method as contemplated herein, that stated for the product as contemplated herein applies mutatis mutandis.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Product for oxidative dyeing of keratin fibres, comprising preparations (A) and (B) prepared separately from one another, wherein
   a first preparation (A) in a cosmetic carrier comprises
   (A1) hydrogen peroxide in a quantity of from 0.5 to 20.0 wt. % relative to the total weight of preparation (A)
   (A2) one or more fatty constituents in a total amount by weight (G1) of from 8.0 to 14.0 wt. % relative to the total weight of preparation (A), wherein preparation (A) comprises as fatty constituent(s) one or more compounds chosen from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons
   (A3) at least one chelating agent chosen from the group of 1-hydroxyethan-1, 1-diphosphonic acid (HEDP), ethylene diamine tetramethylene phosphonic acid (EDTMP), diethylene triamine pentamethylene phosphonic acid (DTPMP), aminotrimethylene phosphonic acid (ATMP), N,N-bis[2-[bis(carboxymethyl)amino] ethyl]glycin, ethylene diamine-N,N'-disuccinic acid (EDDS), 2-hydroxypropylene diamine-N,N'-disuccinic acid (HPDDS), ethylene diamine-N,N'-diglutaric acid (EDDG), ethylene diamine-N,N'-bis-(orthohydroxyphenyl) acetic acid (EDDHA) and/or a physiologically compatible salt thereof, wherein the first preparation (A)—relative to the total weight of preparation (A)—comprises the one or more chelating agents (A3) in a total quantity of from 0.3 to 3.5 wt. % relative to the total weight of preparation (A) and
   (A4) stabilizer selected from the group of 2,6-dipicolinic acid, benzoic acid, salicylic acid, physiologically compatible salts thereof, and combinations thereof, wherein the stabilizer is present in a total quantity of from 0.25 to 0.7 wt. % relative to the total weight of the first preparation (A),
   the second preparation (B) in a cosmetic carrier comprises
   (B1) at least one alkalizing agent and
   (B2) one or more fatty constituents in a total amount by weight (G2) of from 8.0 to 14.0 wt. % relative to the total weight of preparation (B), wherein preparation (B) comprises as fatty constituent(s) one or more compounds chosen from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons,
   the weight ratio (G1)/(G2) has a value of from 0.8 to 1.25
   the first preparation (A) is an aqueous preparation having a pH of from 1.5 to 5.0
   the second preparation (b) is an aqueous preparation having a pH of from 7.5 to 12.5
   the weight ratio (A1)/(A3) has a value of from 3.3 to 13.5
   preparation (A) is prepared in a first container (container A) which comprises three layers, wherein
   an inner layer of container A is polyethylene having a layer thickness of from 20 to 200 μm (micron)
   an outer layer of container A is aluminum having a layer thickness of from 5 to 50 μm and
   a third layer of container A is polyurethane, and
   preparation (B) is prepared in a second container (container B) which comprises three layers, wherein
   an inner layer of container B is polyethylene having a layer thickness of from 20 to 200 μm (micron)
   an outer layer of container B is aluminum having a layer thickness of from 5 to 50 μm and
   a third layer of container B is polyurethane.

2. The product according to claim 1, wherein the first preparation (A)—relative to the total weight of preparation (A)—comprises the one or more chelating agents (A3) in a total quantity of from 0.7 to 2.5 wt. %.

3. The product according to claim 1, wherein
   the first preparation (A) has a viscosity (V1) of from 2000 to 80000 mPas (22° C./Brookfield viscosimeter/spindle 5/4 rpm) and
   the second preparation (B) has a viscosity (V2) of from 2000 to 80000 mPas (22° C./Brookfield viscosimeter/spindle 5/4 rpm).

4. The product according to claim 3, wherein the ratio of the viscosities (V1)/(V2) has a value of from 0.5 to 2.0.

5. The product according to claim 1, wherein
   the first container (container A) and the second container (container B) are together located inside an aerosol pressure container (C), the aerosol pressure container (C) has an outlet opening (D) which is connected to container (A) and to container (B) and the space between the outer walls of the two containers (A) and (B) and the inner wall of the aerosol pressure container (C) is filled with at least one propellant gas.

6. The product according to claim 1, wherein the first preparation (A)—relative to the total weight of preparation (A)—comprises (A1) hydrogen peroxide in a quantity of from 2.5 to 12.0 wt. %.

* * * * *